US00PP36917P2

(12) United States Plant Patent
Bernuetz

(10) Patent No.: US PP36,917 P2
(45) Date of Patent: Sep. 2, 2025

(54) ***XEROCHRYSUM* PLANT NAMED 'Bonxe 1825'**

(50) Latin Name: *Xerochrysum bracteatum*
Varietal Denomination: Bonxe 1825

(71) Applicant: Andrew Bernuetz, Yellow Rock (AU)

(72) Inventor: Andrew Bernuetz, Yellow Rock (AU)

(73) Assignee: BONZA BOTANICALS PTY., LTD., New South Wales (AU)

( * ) Notice: Subject to any disclaimer, the term of this patent is extended or adjusted under 35 U.S.C. 154(b) by 0 days.

(21) Appl. No.: 18/739,248

(22) Filed: Jun. 10, 2024

(51) Int. Cl.
*A01H 5/02* (2018.01)
*A01H 6/14* (2018.01)

(52) U.S. Cl.
USPC ..... Plt./359
CPC ..... *A01H 6/14* (2018.05)

(58) Field of Classification Search
USPC ..... Plt./359
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Xerochrysum* plant named 'Bonxe 1825', characterized by its relatively compact, upright and mounding plant habit; vigorous growth habit; freely branching habit; freely flowering habit; long flowering period; large double type inflorescences with numerous purplish pink-colored involucral bracts; and relatively short and strong peduncles that hold the inflorescences above and beyond the foliar plane.

2 Drawing Sheets

Figure 1:
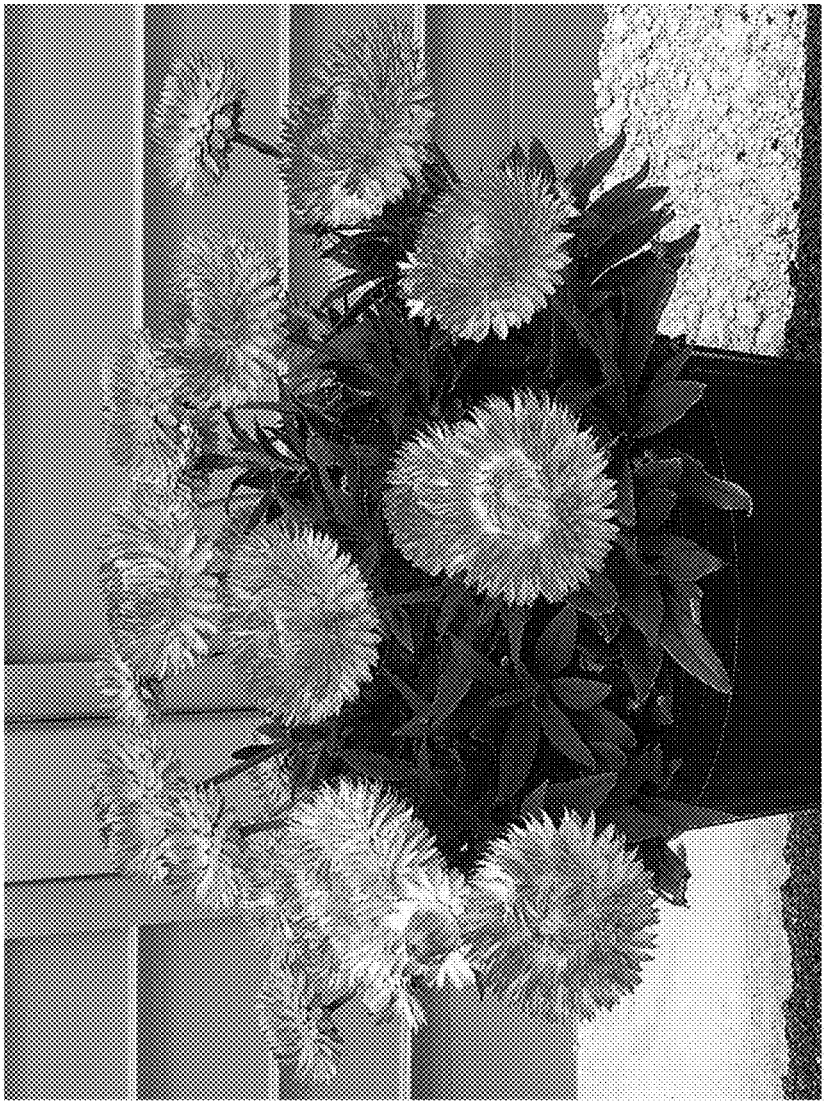

Botanical designation: *Xerochrysum bracteatum.*
Cultivar denomination: 'BONXE 1825'.

BACKGROUND OF THE INVENTION

The present invention relates to a new and distinct cultivar of *Xerochrysum* plant, botanically known as *Xerochrysum bracteatum*, commonly known as Strawflower, and hereinafter referred to by the name 'Bonxe 1825'.

The new *Xerochrysum* plant is a product of a planned breeding program conducted by the Inventor in Yellow Rock, New South Wales, Australia. The objective of the breeding program is to create and develop new upright *Xerochrysum* cultivars with numerous large and attractive inflorescences.

The new *Xerochrysum* plant originated from a cross-pollination by the Inventor in August 2017 of a proprietary selection of *Xerochrysum bracteatum* identified as code number 16-43, not patented, as the female, or seed, parent with a proprietary selection of *Xerochrysum bracteatum* identified as code number 16-38, not patented, as the male, or pollen, parent. The new *Xerochrysum* plant was discovered and selected by the Inventor as a single flowering plant within the progeny of the stated cross-pollination in a controlled greenhouse environment in Yellow Rock, New South Wales, Australia on Feb. 16, 2018.

Asexual reproduction of the new *Xerochrysum* plant by terminal cuttings in a controlled greenhouse environment in Yellow Rock, New South Wales, Australia since February 2018 has shown that the unique features of this new *Xerochrysum* plant are stable and reproduced true to type in successive generations.

SUMMARY OF THE INVENTION

Plants of the new *Xerochrysum* have not been observed under all possible combinations of environmental and cultural conditions. The phenotype may vary somewhat with variations in environment such as temperature and light intensity, without, however, any variance in genotype.

The following traits have been repeatedly observed and are determined to be the unique characteristics of 'Bonxe 1825'. These characteristics in combination distinguish 'Bonxe 1825' as a new and distinct *Xerochrysum* plant:

1. Relatively compact, upright and mounding plant habit.
2. Vigorous growth habit.
3. Freely branching habit.
4. Freely flowering habit.
5. Long flowering period.
6. Large double type inflorescences with numerous purplish pink-colored involucral bracts.
7. Relatively short and strong peduncles that hold the inflorescences above and beyond the foliar plane.

In side-by-side comparisons, plants of the new *Xerochrysum* differ primarily from plants of the female parent selection in involucral bract color as involucral bracts of plants of the new *Xerochrysum* are lighter purplish pink in color than involucral bracts of plants of the female parent selection.

In side-by-side comparisons, plants of the new *Xerochrysum* differ primarily from plants of the male parent selection in involucral bract color as inflorescences of plants of the new *Xerochrysum* have purplish pink-colored involucral bracts whereas inflorescences of plants of the male parent selection have yellow-colored involucral bracts.

Plants of the new *Xerochrysum* can be compared to plants of *Bracteantha bracteata* 'Bonxero 148', disclosed in U.S. Plant Pat. No. 30,398. In side-by-side comparisons, plants of the new *Xerochrysum* differ primarily from plants of 'Bonxero 148' in the following characteristics:

1. Plants of the new *Xerochrysum* are more compact than plants of 'Bonxero 148'.

2. Plants of the new *Xerochrysum* are not as upright as plants of 'Bonxero 148'.
3. Plants of the new *Xerochrysum* are more freely branching than plants of 'Bonxero 148'.
4. Inflorescences of plants of the new *Xerochrysum* have more involucral bracts than inflorescences of plants of 'Bonxero 148'.
5. Inflorescences of plants of the new *Xerochrysum* have purplish pink-colored involucral bracts whereas inflorescences of plants of 'Bonxero 148' have bright yellow-colored involucral bracts.
6. Plants of the new *Xerochrysum* have shorter peduncles than plants of 'Bonxero 148'.

BRIEF DESCRIPTION OF THE PHOTOGRAPHS

The accompanying photographs illustrate the overall appearance of the new *Xerochrysum* plant. These photographs show the colors as true as it is reasonably possible to obtain in colored reproductions of this type. Colors in the photographs may differ slightly from the color values cited in the detailed botanical description which accurately describe the colors of the new *Xerochrysum* plant.

The photograph on the first sheet (FIG. 1) is a side perspective view of a typical flowering plant of 'Bonxe 1825' grown in a container.

Figure 2:
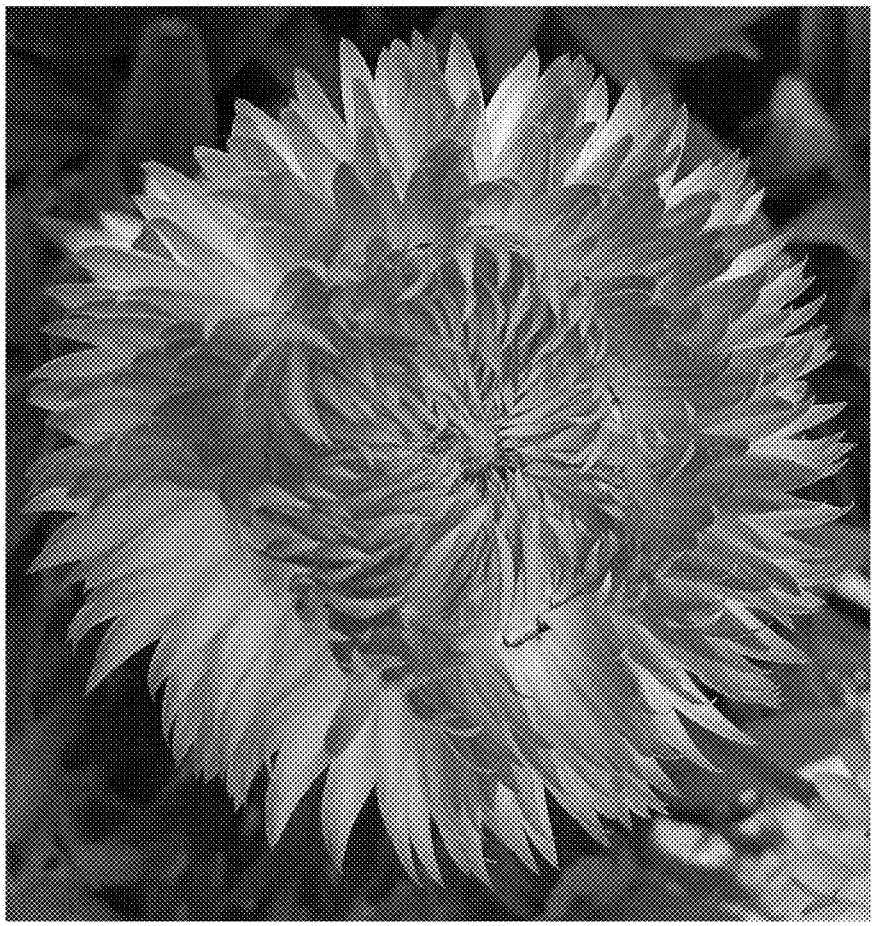

The photograph on the second sheet (FIG. 2) is a close-up view of a typical inflorescence of 'Bonxe 1825'.

DETAILED BOTANICAL DESCRIPTION

The aforementioned photographs and following observations and measurements describe plants grown during the summer in 24-cm containers in an outdoor nursery in Higashiomi, Shiga, Japan and under conditions and practices which approximate those generally used in commercial *Xerochrysum* production. During the production of the plants, day temperatures averaged 23° C. and night averaged 13° C. Plants were four months old when the photographs were taken and five months old when the detailed description was taken. Measurements and numerical values represent averages for typical flowering plants. In the following description, color references are made to The Royal Horticultural Society Colour Chart, 2015 Edition, except where general terms of ordinary dictionary significance are used.

Botanical classification: *Xerochrysum bracteatum* 'Bonxe 1825'.

Parentage:

*Female, or seed, parent*.—Proprietary selection of *Xerochrysum bracteatum* identified as code number 16-43, not patented.

*Male, or pollen, parent*.—Proprietary selection of *Xerochrysum bracteatum* identified as code number 16-38, not patented.

Propagation:

*Type*.—Terminal vegetative cuttings.

*Time to initiate roots, summer*.—About seven days at temperatures about 18° C. to 21° C.

*Time to initiate roots, winter*.—About ten days at temperatures about 18° C. to 21° C.

*Time to produce a rooted cutting, summer*.—About three weeks at temperatures about 18° C. to 21° C.

*Time to produce a rooted cutting, winter*.—About four weeks at temperatures about 18° C. to 21° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant form and growth habit*.—Relatively compact, upright and mounding plant habit with inflorescences held above the foliage on strong peduncles; vigorous growth habit.

*Plant height*.—About 35 cm.

*Plant diameter or spread*.—About 56 cm.

*Lateral branches*.—Quantity per plant: Freely branching habit with about 22 primary lateral branches with numerous secondary lateral branches developing per plant. Length: About 19.8 cm. Diameter: About 4.5 mm. Internode length: About 9 mm. Aspect: Mostly upright to outwardly. Strength: Strong. Texture: Moderately pubescent. Color: Close to 138B.

*Leaf description*.—Arrangement: Alternate, simple; sessile. Length: About 7.6 cm. Width: About 1.8 cm. Shape: Linear. Apex: Acuminate. Base: Attenuate. Margin: Entire; not undulate to slightly undulate. Texture, upper and lower surfaces: Rough, moderately pubescent. Venation pattern: Pinnate; reticulate. Color: Developing leaves, upper surface: Close to 137A. Developing leaves, lower surface: Close to 137B. Fully expanded leaves, upper surface: Close to NN137A; venation, close to 138B. Fully expanded leaves, lower surface: Close to NN137B; venation, close to 138C.

*Inflorescence description*.—Appearance: Terminal double type inflorescence form with numerous ovate-shaped involucral bracts; inflorescences convex in cross-section; involucral bracts and disc florets developing acropetally on a capitulum; inflorescences positioned above the foliar plane on strong peduncles; inflorescences face mostly upright. Flowering habit: Freely flowering habit; about 27 inflorescence buds and inflorescences develop per plant during the flowering season. Fragrance: None detected. Time to flower: In Japan, plants begin to flower about 21 weeks after planting and in the garden, plants flower continuously from the spring until late autumn. Post-production longevity: Inflorescences maintain good substance for about seven to ten days on the plant; inflorescences persistent.

*Inflorescence buds*.—Height: About 1.8 cm. Diameter: About 1.1 cm. Shape: Ovoid with acute apex. Color: Proximally, close to 195D and distally, close to 60B.

*Inflorescence size*.—Diameter: About 6.7 cm. Depth (height): About 2.8 cm. Disc diameter: About 2.9 cm. Disc height: About 1.2 cm.

*Receptacles*.—Diameter: About 3.5 cm. Height: About 6.6 mm. Color: Close to 145D.

*Involucral bracts*.—Quantity per inflorescence and arrangement: About 830 arranged in numerous whorls; bracts imbricate. Length: About 1.9 cm. Width: About 7 mm. Shape: Ovate. Apex: Acuminate. Base: Truncate. Margin: Entire. Texture, upper and lower surfaces: Smooth, glabrous; papery; durable. Orientation: Initially upright becoming more outward with development. Color: When opening and fully opened, upper surface: Close to 63C; color does not change with subsequent development.

When opening and fully opened, lower surface: Close to 63D; color does not change with subsequent development.

*Disc florets*.—Quantity per inflorescence and arrangement: Numerous disc florets are spirally arranged in the center of the receptacle. Length: About 9 mm. Diameter, distally: About 1.5 mm. Diameter, proximally: About 0.8 mm. Shape: Tubular; apex dentate, five-pointed. Texture, inner and outer surfaces: Smooth, glabrous. Color: Apex: Close to 17A. Midsection and base: Close to 145C.

*Peduncles*.—Length: About 7.4 cm. Diameter: About 3 mm. Strength: Strong. Aspect: Mostly upright. Texture: Rough, pubescent. Color: Close to 138B.

*Reproductive organs*.—Androecium: Quantity per disc floret: About five. Filament length: About 7.4 mm. Filament color: Close to 145D. Anther size: About 0.8 mm by 2.4 mm. Anther shape: Linear. Anther color: Close to 17B. Pollen amount: None observed. Gynoecium: Quantity per disc floret: One. Pistil length: About 9.2 mm. Stigma shape: Bi-parted. Stigma color: Close to 17B. Style color: Close to 157D. Ovary color: Close to 155A.

*Seeds and fruits*.—To date, seed and fruit production has not been observed on plants of the new *Xerochrysum*.

Pathogen & pest resistance: To date, plants of the new *Xerochrysum* have not been observed to be resistant to pathogens and pests common to *Xerochrysum* plants.

Temperature tolerance: Plants of the new *Xerochrysum* have been observed to tolerate temperatures ranging from about 1° C. to about 35° C.

It is claimed:

1. A new and distinct *Xerochrysum* plant named 'Bonxe 1825' as herein illustrated and described.

* * * * *